United States Patent [19]

Lubisch et al.

[11] Patent Number: 5,175,174
[45] Date of Patent: Dec. 29, 1992

[54] PHENYLPIPERIDINYLAMINES AND DRUGS CONTAINING THESE

[75] Inventors: Wilfried Lubisch, Mannheim; Sabine Schult, Heidelberg; Rudolf Binder, Worms; Manfred Raschack, Weisenheim am Sand; Roland Reinhardt, Kaiserslautern; Dietmar Seemann, Nussloch, all of Fed. Rep. of Germany

[73] Assignee: BASF Aktiengesellschaft, Ludwigshafen, Fed. Rep. of Germany

[21] Appl. No.: 760,158

[22] Filed: Sep. 16, 1991

[30] Foreign Application Priority Data

Oct. 16, 1990 [DE] Fed. Rep. of Germany ....... 4032767

[51] Int. Cl.⁵ .................. A61K 31/445; C07D 211/56; C07D 211/98
[52] U.S. Cl. .................................. 514/318; 514/326; 514/329; 546/194; 546/208; 546/223
[58] Field of Search ............... 546/223, 208, 194, 193; 514/318, 326, 329

[56] References Cited

U.S. PATENT DOCUMENTS 3,468,892  9/1969  Tomcufcik ........................ 546/223
4,902,800  2/1990  Skotnicki ............................ 546/208

FOREIGN PATENT DOCUMENTS 97000  12/1983  European Pat. Off. ........... 546/223
291210  11/1988  European Pat. Off. ........... 546/194
749887  5/1943  Fed. Rep. of Germany.

OTHER PUBLICATIONS

Berichte Der Deutschen Chemischen Gesellschaft, 74, 1941, pp. 1648–1663, E. Cerkovnikov, et al., "Uber Eine Neue Reihe".

Helvetica Chimica Acta, vol. 26, 1943, pp. 1132–1143, V. Hahn, et al., "Uber Substituierte 4-Amino-Piperidine".

Primary Examiner—C. Warren Ivy
Assistant Examiner—Celia Chang
Attorney, Agent, or Firm—Oblon, Spivak, McClelland, Maier & Neustadt

[57] ABSTRACT

Phenylpiperidinylamines of the formula I

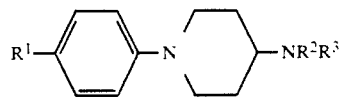

where
$R^1$ is $-NHSO_2R^4$ or

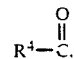

$R^2$ and $R^3$ are each, independently of one another, H or $C_1-C_4$-alkyl or together are a $(CH_2)_n$ chain with $n=4$ or 5, and
$R^4$ is $C_1-C_4$-alkyl or phenyl, and the physiologically tolerated salts thereof, and pharmaceutical compositions containing these are described.

2 Claims, No Drawings

PHENYLPIPERIDINYLAMINES AND DRUGS CONTAINING THESE

The present invention relates to phenylpiperidinylamine derivatives of the formula I and to drugs containing these, especially for use as class III antiarrhythmics and as receptors.

Phenylpiperidinylamines are described in BE 678 063 (antiproteolytic action) and U.S. Pat. No. 4,902,800 (interleukin-1 inhibitor). Furthermore, phenylpiperidinylamines with an antihistamine action have been described in DRP 749 887 (1941); E. Cerkovnikow et al., Chem. Ber. 74 (1941) 1648, 1658 and 1661, and V. Hahn et al., Helv. Chim. Acta 26 (1943) 1132.

It is an object of the present invention to develop novel Vaughan Williams class III antiarrhythmics (Mechanisms and Treatment of Cardiac Arrhythmias; Edit. H. J. Reiser and L. N. Horowitz, Verlag Urban und Schwarzenberg, Baltimore and Munich 1985, chapter II.C) with improved properties.

We have found that this object is achieved by phenylpiperidinylamines of the formula I

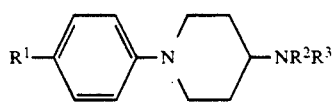

I where
R$^1$ is —NHSO$_2$R$^4$ or

R$^2$ and R$^3$ are each, independently of one another, H or C$_1$-C$_4$-alkyl or together are a (CH$_2$)$_n$ chain with n=4 or 5, and R$^4$ is C$_1$-C$_4$-alkyl or phenyl, and the physiologically tolerated salts thereof and drugs containing these.

The compounds according to the invention can be prepared by the following processes:

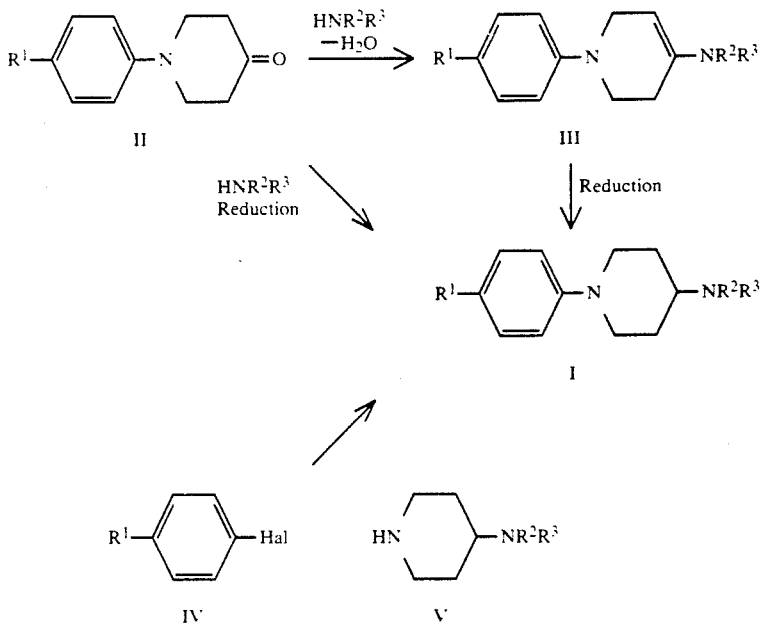

The piperidone II (Synthesis 1981, 606–608) is converted at elevated temperature with acid catalysis, e.g. with p-toluenesulfonic acid and formic acid, in an aprotic solvent, preferably toluene, with elimination of water into the enamine III which can be converted by reduction with, for example, sodium borohydride or hydrogen/Pd/carbon in conventional solvents such as alcohols into the compounds I according to the invention. I is likewise obtained by direct reaction of the piperidones II with amines HNR$^2$R$^3$ dissolved in conventional solvents, preferably alcohols, under reductive conditions, e.g. in the presence of sodium cyanoborohydride or hydrogen/Pd/carbon. Starting from the aromatic halide IV (Hal=F, Cl, Br) reaction with the amine V in, preferably, polar media such as alcohols and dimethylformamide in the presence of bases such as potassium carbonate at elevated temperature, preferably 50°–150° C., likewise gives I.

The phenylpiperidinylamines obtained in this way are, where appropriate, converted into the salt with a physiologically tolerated acid. A list of conventional physiologically tolerated acids can be found, for example, in Fortschritte der Arzneimittelforschung, 1966, Birkhäuser Verlag, Vol. 10, pages 244 to 285, Germany, Switzerland.

The acid addition salts are usually obtained in a conventional manner by mixing the free base or solutions thereof with the appropriate acid or solutions thereof in an organic solvent, for example a lower alcohol such as methanol, ethanol or propanol, or a lower ketone such as acetone, methyl ethyl ketone or methyl isobutyl ketone, or an ether such as diethyl ether, tetrahydrofuran or dioxane. Mixtures of such solvents can be used to improve crystallization In addition, it is possible to prepare pharmaceutically acceptable aqueous solutions of acid addition compounds of the phenylpiperidinylamines of the formula I by dissolving the free base in an aqueous solution of the acid.

The phenylpiperidinylamines according to the invention are class III antiarrhythmics. In addition, they have affinity for the receptor and thus represent potential antipsychotics, anticonvulsants and neuroprotectives (cf. F. C. Tortella TIBS 10 (1989) 501 et seq.). We have also found that the compounds block the ATP-sensitive K channel (cf. Ann. Rev. Neuroscience 11 (1988) 97-118).

Hence the present invention also relates to therapeutic agents for topical and, especially, systemic administration, which contain a compound of the formula I as active substance in addition to conventional carriers and/or other pharmaceutical auxiliaries.

The therapeutic agents or compositions are prepared using conventional liquid or solid carriers or diluents and the auxiliaries conventionally used in pharmaceutical technology, appropriate for the required mode of administration and in a dosage suitable for administration, in a conventional manner, for example by mixing the active substance with the solid or liquid carriers and auxiliaries conventional in such products.

The agents can be administered orally, parenterally or topically. Examples of compositions of these types are uncoated or (film-)coated tablets, capsules, pills, powders, solutions or suspensions, infusion or injection solutions, and pastes, ointments, gels, creams, lotions, dusting powders, solutions or emulsions and sprays.

The therapeutic agents can contain the compounds to be used according to the invention in a concentration of from 0.01 to 1% for topical administration and preferably in a single dose of from 0.1 to 25 mg per kg of body weight for systemic administration, and can be administered in one or more dosages each day depending on the nature and severity of the disorders.

Examples of auxiliaries conventionally used in pharmaceutical technology are, for topical administration, alcohols such as ethanol, isopropanol, ethoxylated castor oil or ethoxylated hydrogenated castor oil, polyacrylic acid, glycerol monostearate, liquid paraffin, petrolatum, lanolin, polyethylene glycol, polypropylene glycol, stearate and ethoxylated fatty alcohol, and, for systemic administration, lactose, propylene glycol and ethanol, starch, talc and polyvinylpyrrolidone. It is possible, where appropriate, to add to the products an antioxidant, for example tocopherol and butylated hydroxyanisole or butylated hydroxytoluene, or flavorings, stabilizers, emulsifiers, bleaches etc. It is a requirement that all the substances used in the preparation of pharmaceutical compositions are toxicologically innocuous and compatible with the active substances used.

STARTING MATERIALS

Preparation 1

1.4 g (22.7 mmol) of sodium cyanoborohydride were added a little at a time to 5.0 g (22.7 mmol) of 1-(4-nitrophenyl)-4-piperidone, 1.4 g (22.7 mmol) of acetic acid and 3.4 g (45.4 mmol) of diethylamine in 200 ml of methanol at room temperature. The mixture was left to stir for 16 h and then the solvent was removed under reduced pressure. The residue was partitioned between ethyl acetate and water, and the organic phase was dried and concentrated under reduced pressure. The resulting product was taken up in acetone and precipitated with ethereal hydrogen chloride solution to give 4-(N,N-diethylamino)-1-(4-nitrophenyl)piperidine hydrochloride. Melting point 183°-184° C.

Preparation 2

5.0 g (22.7 mmol) of 1-(4-nitrophenyl)-4-piperidone, 16.0 g (220 mmol) of diethylamine and 5 ml of formic acid in 150 ml of toluene were refluxed with a water trap for 5 h. The solvent was removed under reduced pressure, and 4-(N,N-diethylamino)-1-(4-nitrophenyl)-1,2,3,6-tetrahydropyridine was obtained as crude product. 3.45 g (92.5 mmol) of sodium borohydride were added a little at a time to this crude product in 150 ml of ethanol at 10° C. The mixture was left to stir at room temperature for 3 h and then the solvent was removed under reduced pressure. The residue was partitioned between water and methylene chloride, and the organic phase was dried and concentrated under reduced pressure. This crude product was dissolved in a little isopropanol, and ethereal hydrogen chloride solution was added to give 5.5 g of 4-(N,N-diethylamino)-1-(4-nitrophenyl)piperidine hydrochloride, which was identical to the product from preparation 1. Melting point 183°-184° C.

EXAMPLE 1

5.0 g (20.2 mmol) of the product from preparation 1 was hydrogenated on Pd/carbon in methanol in a conventional manner to give 1-(4-aminophenyl)-4-(N,N-diethylamino)piperidine.

2.4 g (21 mmol) of methanesulfonyl chloride dissolved in 10 ml of tetrahydrofuran were added dropwise to 4.4 g (20.2 mmol) of this product and 1.7 g (21 mmol) of pyridine in 100 ml of anhydrous tetrahydrofuran at 0°-5° C. The mixture was left to stir at room temperature for 6 h and the precipitated product was separated off to give 4-(N,N-diethylamino)-1-(4-methanesulfonylaminophenyl]piperidine. Melting point 214°-215° C.

EXAMPLE 2

2.1 g (13.25 mmol) of 4-(N,N-diethylamino)piperidine, 1.8 g (13.25 mmol) of 4-fluoroacetophenone and 7.3 g of potassium carbonate in 100 ml of dimethylformamide/n-propanol (1:1) were refluxed for 20 h. 1.9 g of 1-(4-acetylphenyl)-4-(N,N-diethylamino)piperidine were obtained as crystalline fumarate. Melting point 125°-127° C.

We claim:

1. A phenylpiperidinylamine of the formula I

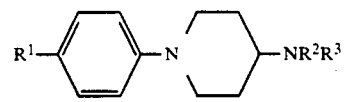

where
R$^1$ is —NHSO$_2$R$^4$ or

R$^2$ and R$^3$ are each, independently of one another, H or C$_1$-C$_4$-alkyl or together are a (CH$_2$)$_n$ chain with n=4 or 5, and
R$^4$ is C$_1$-C$_4$-alkyl or phenyl, or a physiologically tolerated salt thereof.

2. An antiarrhythmic pharmaceutical composition which contains from 7 to 1750 mg of a compound as claimed in claim 1 per dose, in admixture with a pharmaceutically acceptable inert auxiliary.

* * * * *